United States Patent
Morikazu (10) Patent No.: US 9,233,433 B2
(45) Date of Patent: Jan. 12, 2016

(54) LASER PROCESSING METHOD AND LASER PROCESSING APPARATUS

(71) Applicant: Disco Corporation, Tokyo (JP)

(72) Inventor: Hiroshi Morikazu, Tokyo (JP)

(73) Assignee: DISCO CORPORATION, Tokyo (JP)

( * ) Notice: Subject to any disclaimer, the term of this patent is extended or adjusted under 35 U.S.C. 154(b) by 270 days.

(21) Appl. No.: 13/764,889

(22) Filed: Feb. 12, 2013

(65) Prior Publication Data

US 2013/0213946 A1    Aug. 22, 2013

(30) Foreign Application Priority Data

Feb. 20, 2012    (JP) .................................. 2012-033757

(51) Int. Cl.
*B23K 26/40* (2014.01)
*G01N 21/71* (2006.01)
*B23K 26/00* (2014.01)
*B23K 26/36* (2014.01)

(52) U.S. Cl.
CPC ........... *B23K 26/0066* (2013.01); *B23K 26/367* (2013.01); *B23K 26/4075* (2013.01); *B23K 26/4085* (2013.01); *G01N 21/718* (2013.01)

(58) Field of Classification Search
CPC ............. B23K 26/0066; B23K 26/367; B23K 26/4075; B23K 26/0048; G01N 21/718
See application file for complete search history.

(56) References Cited

U.S. PATENT DOCUMENTS

| | | | |
|---|---|---|---|
| 6,804,574 B2* | 10/2004 | Liu et al. ...................... 700/166 |
| 2005/0011867 A1* | 1/2005 | Okuda et al. ............. 219/121.63 |
| 2008/0192250 A1* | 8/2008 | Yoo et al. ...................... 356/326 |
| 2009/0127233 A1* | 5/2009 | Asano et al. ............... 219/121.7 |
| 2009/0242018 A1* | 10/2009 | Ahn et al. ...................... 136/255 |
| 2011/0100967 A1* | 5/2011 | Yoo et al. ................. 219/121.83 |
| 2011/0195537 A1* | 8/2011 | Koyanagi et al. ............... 438/33 |
| 2011/0284510 A1* | 11/2011 | Reeves-Hall et al. ..... 219/121.72 |
| 2012/0000893 A1* | 1/2012 | Broude et al. ............ 219/121.68 |
| 2013/0153015 A1* | 6/2013 | Lee et al. ...................... 136/256 |
| 2013/0153552 A1* | 6/2013 | Jeong et al. .............. 219/121.69 |

FOREIGN PATENT DOCUMENTS

| JP | 2005-118832 | 5/2005 |
|---|---|---|
| WO | WO-02/29853 A2 * | 4/2002 |
| WO | WO-02/35595 A1 * | 5/2002 |

OTHER PUBLICATIONS

Tong et al., "Reak-time control of ultrafast laser micromachining by laser-induced breakdown spectroscopy", Mar. 2004, Applied Optics, vol. 43, No. 9, pp. 1971-1980.*

* cited by examiner

*Primary Examiner* — Geoffrey S Evans
(74) *Attorney, Agent, or Firm* — Greer Burns & Crain, Ltd.

(57) ABSTRACT

A laser processing method of applying a laser beam to a workpiece having a plurality of members, thereby forming a laser processed groove on the workpiece. The laser processing method includes the steps of setting a plurality of processing conditions respectively corresponding to a plurality of different materials forming the plurality of members constituting the workpiece, detecting the wavelengths of plasma lights generated by applying the laser beam to the plurality of members constituting the workpiece, selecting any suitable one of the processing conditions corresponding to any one of the members corresponding to the wavelength of plasma lights detected above, and applying the laser beam under the processing condition selected above.

3 Claims, 7 Drawing Sheets

Processing conditions map

| Material | Repetition frequency (KHz) | Power (W) |
|---|---|---|
| Si | 200 | 3 |
| Cu | 100 | 2 |
| SiO₂ | 200 | 1 |
| Al | 100 | 1 |

LASER PROCESSING METHOD AND LASER PROCESSING APPARATUS

BACKGROUND OF THE INVENTION

1. Field of the Invention

The present invention relates to a laser processing method and apparatus for applying a laser beam to a workpiece having a plurality of members to thereby form a laser processed groove on the workpiece.

2. Description of the Related Art

As well known in the art, in a semiconductor device fabrication process, a plurality of crossing division lines called streets are formed on the front side of a substantially disk-shaped semiconductor substrate to thereby partition a plurality of regions where a plurality of devices such as ICs and LSIs are respectively formed, thus constituting a semiconductor wafer. The semiconductor wafer is cut along the streets to thereby obtain the individual semiconductor devices. Cutting of the semiconductor wafer along the streets is usually performed by using a cutting apparatus. This cutting apparatus includes a chuck table for holding the semiconductor wafer as a workpiece, cutting means for cutting the semiconductor wafer held on the chuck table, and moving means for relatively moving the chuck table and the cutting means. The cutting means includes a spindle adapted to be rotated at high speeds and a cutting blade mounted on the spindle. The cutting blade is composed of a disk-shaped base and an annular cutting edge mounted on a side surface of the base along the outer circumference thereof. The cutting edge is formed by bonding diamond abrasive grains having a grain size of about 3 μm by electroforming so that the thickness of the cutting edge becomes about 20 μm, for example.

In recent years, a semiconductor wafer intended to improve the processing performance of devices such as ICs and LSIs has been put into practical use. This semiconductor wafer is composed of a semiconductor substrate such as a silicon wafer and a low-permittivity insulator film (Low-k film) formed on the front side of the semiconductor substrate. Examples of the Low-k film include an inorganic film of SiOF, BSG (SiOB), etc. and an organic film such as a polymer film of polyimide, parylene, etc.

Further, there has been put into practical use a semiconductor wafer having a configuration such that a plurality of testing metal patterns called test element group (Teg) for testing the function of the devices are partially provided on the Low-k film in the streets.

However, the Low-k film is formed as a multilayer film like mica and it is very brittle. Accordingly, when this semiconductor wafer having the Low-k film is cut along the streets by using the cutting blade, there arises a problem such that the Low-k film may be separated and this separation may reach the devices to cause fatal damage to the semiconductor devices. Further, in the case of the semiconductor wafer such that the testing metal patterns called test element group (Teg) for testing the function of the devices are partially provided on the streets, there arises a problem such that when the semiconductor wafer is cut along the streets by using the cutting blade, burrs may be generated because the metal patterns are formed of a tough metal such as copper, causing chipping on the side surfaces of each device to result in a degradation in quality of each device.

To solve the above problems, there has been proposed a wafer dividing method including the steps of applying a laser beam to the semiconductor wafer along each street to form a laser processed groove along each street, thereby removing the Low-k film and the Teg on each street and next cutting this area where the Low-k film and the Teg have been removed, by using a cutting blade. However, in the case that the Low-k film and the Teg are provided on each street, the Low-k film and the Teg are removed by applying the laser beam under different processing conditions. Accordingly, this wafer dividing method includes a Teg removing step of preliminarily detecting the position of the Teg to make coordinate data and then applying a laser beam to the Teg according to this coordinate data to thereby remove the Teg and a Low-k film removing step of applying the laser beam to the Low-k film on each street to thereby remove the Low-k film (see Japanese Patent Laid-Open No. 2005-118832, for example).

SUMMARY OF THE INVENTION

The technique disclosed in Japanese Patent Laid-Open No. 2005-118832 has a problem such that the position of the Teg must be preliminarily detected to make coordinate data, causing a reduction in productivity. Further, in feeding the holding means for holding the wafer, the position of the holding means is compared with the coordinate data to control the processing conditions. Accordingly, if there is a deviation between the position of the holding means and the coordinate data, the Teg and the Low-k film cannot be processed under proper processing conditions.

It is therefore an object of the present invention to provide a laser processing method and apparatus which can perform laser processing under the processing conditions individually suitable for two or more kinds of members mixedly present in a subject area of the workpiece to be laser-processed, without making coordinate data for each member.

In accordance with an aspect of the present invention, there is provided a laser processing method of applying a laser beam to a workpiece having a plurality of members, thereby forming a laser processed groove on the workpiece, the laser processing method including a processing conditions setting step of setting a plurality of processing conditions respectively corresponding to a plurality of different materials forming the plurality of members constituting the workpiece; a wavelength detecting step of detecting the wavelengths of plasma lights generated by applying the laser beam to the plurality of members constituting the workpiece; a processing condition selecting step of selecting any suitable one of the processing conditions corresponding to any one of the members corresponding to the wavelength of plasma lights detected by the wavelength detecting step; and a laser processing step of applying the laser beam to the workpiece under the processing condition selected by the processing condition selecting step, thereby forming the laser processed groove on the workpiece.

In accordance with another aspect of the present invention, there is provided a laser processing apparatus including workpiece holding means for holding a workpiece; laser beam applying means for applying a laser beam to the workpiece held by the workpiece holding means, the laser beam applying means including laser beam oscillating means for oscillating a laser beam, power adjusting means for adjusting the power of the laser beam oscillated by the laser beam oscillating means, and focusing means for focusing the laser beam adjusted in power by the power adjusting means; feeding means for relatively feeding the workpiece holding means and the laser beam applying means; plasma detecting means for detecting the wavelength of plasma light generated by applying the laser beam from the laser beam applying means to the workpiece held by the wavelength holding means; and control means for controlling the laser beam applying means according to a detection signal from the plasma detecting means; the plasma detecting means including branching means for branching the plasma light into a plurality of optical paths; a plurality of bandpass filters respectively provided on the plurality of optical paths for respectively passing only the specific wavelengths of plasma lights generated from a plurality of different materials forming a plurality of members constituting the workpiece; and a plurality of photodetectors for respectively detecting the lights passed through the plurality of bandpass filters and outputting light intensity signals to the control means; the control means having a memory storing a processing conditions map setting a plurality of processing conditions respectively corresponding to the plurality of different materials; the control means selecting any suitable one of the processing conditions set on the processing conditions map according to the detection signals from the plurality of photodetectors and then controlling the laser beam applying means under the processing condition selected above.

Preferably, the processing conditions map sets a plurality of powers of the laser beam respectively corresponding to the plurality of different materials; and the control means controls the power adjusting means so that the power of the laser beam becomes a suitable one of the powers set on the processing conditions map according to the detection signals from the plurality of photodetectors.

Preferably, the laser beam oscillating means includes a pulsed laser oscillator for oscillating a pulsed laser beam and repetition frequency setting means for setting the repetition frequency of the pulsed laser beam to be oscillated by the pulsed laser oscillator; the processing conditions map sets a plurality of repetition frequencies of the pulsed laser beam corresponding to the plurality of different materials; and the control means controls the repetition frequency setting means so that the repetition frequency of the pulsed laser beam becomes a suitable one of the repetition frequencies set on the processing conditions map according to the detection signals from the plurality of photodetectors.

As described above, the laser processing method of applying a laser beam to a workpiece having a plurality of members, thereby forming a laser processed groove on the workpiece according to the present invention includes the steps of setting a plurality of processing conditions respectively corresponding to a plurality of different materials forming the plurality of members constituting the workpiece, detecting the wavelengths of plasma lights generated by applying the laser beam to the plurality of members constituting the workpiece, selecting any suitable one of the processing conditions corresponding to any one of the members corresponding to the wavelength of the plasma light detected above, and applying the laser beam under the processing condition selected above. Thus, the applying means is controlled. Accordingly, even in the case that two or more kinds of members are mixedly present in a subject area of the workpiece to be laser-processed, laser processing can be performed to the workpiece under the processing conditions individually suitable for the plural members every time the pulsed laser beam is applied to each member to generate the plasma light having the specific wavelength corresponding to each member.

As described above, the laser processing apparatus according to the present invention includes the plasma detecting means for detecting the wavelength of plasma light generated by applying the laser beam to the workpiece held by the workpiece holding means and the control means for controlling the laser beam applying means according to the detection signal from the plasma detecting means. The plasma detecting means includes the branching means for branching the plasma light into the plural optical paths, the plural bandpass filters respectively provided on the plural optical paths for respectively passing only the specific wavelengths of plasma lights generated from the plural different materials forming the plural members constituting the workpiece, and the plural photodetectors for respectively detecting the lights passed through the plural bandpass filters and outputting the respective light intensity signals to the control means. The control means has the memory storing the processing conditions map setting the plural processing conditions respectively corresponding to the plural different materials mentioned above. The control means selects any suitable one of the plural processing conditions set on the processing conditions map according to the detection signals from the plural photodetectors and then controls the laser beam applying means under the processing condition selected above. Accordingly, even in the case that two or more kinds of members are mixedly present in a subject area of the workpiece to be laser-processed, laser processing can be performed to the workpiece by the control means under the processing conditions individually suitable for the plural members every time the pulsed laser beam is applied to each member to generate the plasma light having the specific wavelength corresponding to each member.

The above and other objects, features and advantages of the present invention and the manner of realizing them will become more apparent, and the invention itself will best be understood from a study of the following description and appended claims with reference to the attached drawings showing some preferred embodiments of the invention.

DETAILED DESCRIPTION OF THE PREFERRED EMBODIMENTS

Figure 1:
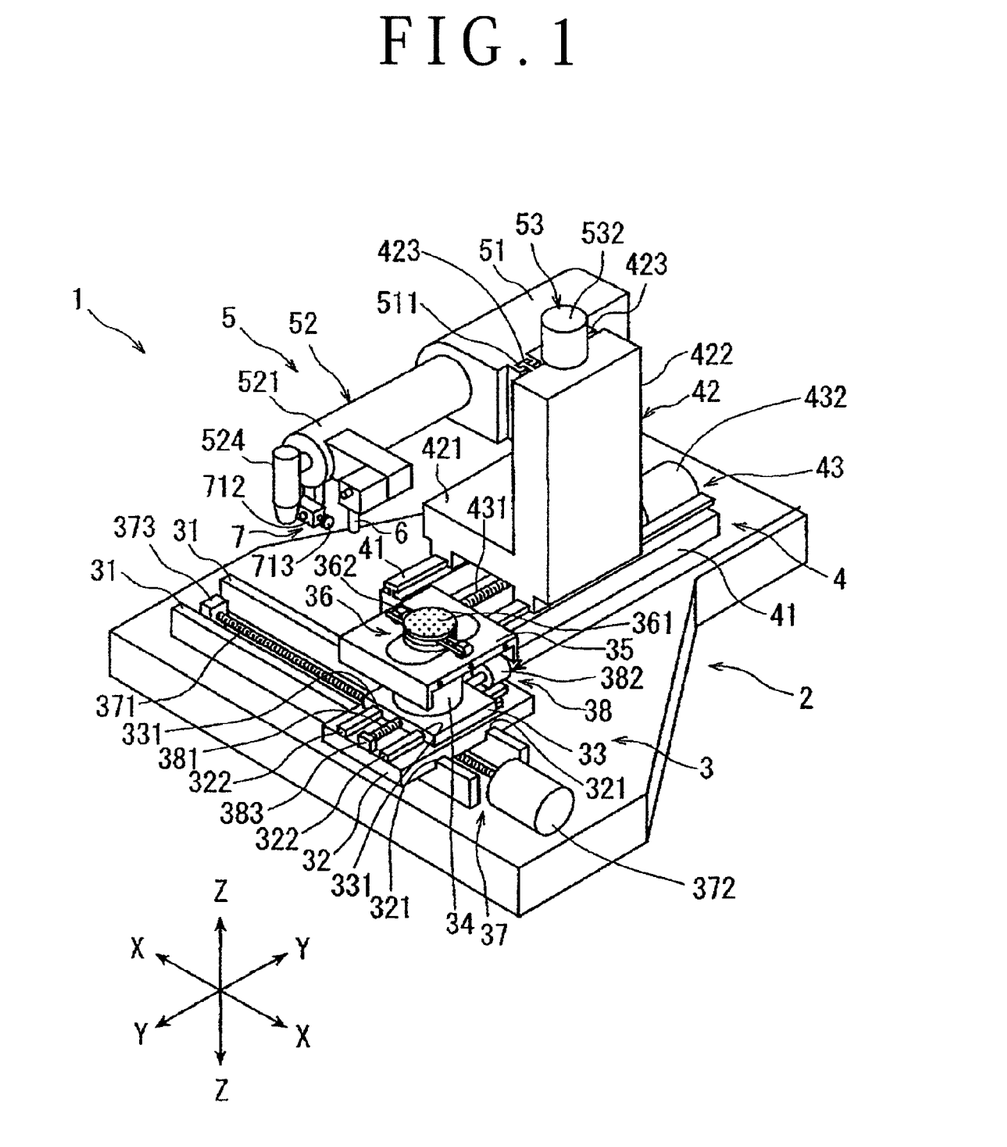
FIG. 1 is a perspective view of a laser processing apparatus according to a preferred embodiment of the present invention.

A preferred embodiment of the laser processing method and apparatus according to the present invention will now be described in detail with reference to the attached drawings. FIG. 1 is a perspective view of a laser processing apparatus according to a preferred embodiment of the present invention. The laser processing apparatus 1 shown in FIG. 1 includes a stationary base 2, a chuck table mechanism 3 for holding a workpiece, the chuck table mechanism 3 being provided on the stationary base 2 so as to be movable in a feeding direction (X direction) shown by an arrow X, a laser beam applying unit supporting mechanism 4 provided on the stationary base 2 so as to be movable in an indexing direction (Y direction) shown by an arrow Y perpendicular to the X direction, and a laser beam applying unit 5 provided on the laser beam applying unit supporting mechanism 4 so as to be movable in a focal position adjusting direction (Z direction) shown by an arrow Z.

The chuck table mechanism 3 includes a pair of guide rails 31 provided on the stationary base 2 so as to extend parallel to each other in the X direction, a first slide block 32 provided on the guide rails 31 so as to be movable in the X direction, a second slide block 33 provided on the first slide block 32 so as to be movable in the Y direction, a cover table 35 supported by a cylindrical member 34 standing on the second slide block 33, and a chuck table 36 as workpiece holding means. The chuck table 36 has a vacuum chuck 361 formed of a porous material. A workpiece such as a disk-shaped semiconductor wafer is adapted to be held under suction on the vacuum chuck 361 by operating suction means (not shown). The chuck table 36 is rotatable by a pulse motor (not shown) provided in the cylindrical member 34. Further, the chuck table 36 is provided with clamps 362 for fixing an annular frame to be hereinafter described.

The lower surface of the first slide block 32 is formed with a pair of guided grooves 321 for slidably engaging the pair of guide rails 31 mentioned above. A pair of guide rails 322 are provided on the upper surface of the first slide block 32 so as to extend parallel to each other in the Y direction. Accordingly, the first slide block 32 is movable in the X direction along the guide rails 31 by the slidable engagement of the guided grooves 321 with the guide rails 31. The chuck table mechanism 3 further includes feeding means 37 (X direction moving means) for moving the first slide block 32 in the X direction along the guide rails 31. The feeding means 37 includes an externally threaded rod 371 extending parallel to the guide rails 31 so as to be interposed therebetween and a pulse motor 372 as a drive source for rotationally driving the externally threaded rod 371. The externally threaded rod 371 is rotatably supported at one end thereof to a bearing block 373 fixed to the stationary base 2 and is connected at the other end to the output shaft of the pulse motor 372 so as to receive the torque thereof. The externally threaded rod 371 is engaged with a tapped through hole formed in an internally threaded block (not shown) projecting from the lower surface of the first slide block 32 at a central portion thereof. Accordingly, the first slide block 32 is moved in the X direction along the guide rails 31 by operating the pulse motor 372 to normally or reversely rotate the externally threaded rod 371.

The lower surface of the second slide block 33 is formed with a pair of guided grooves 331 for slidably engaging the pair of guide rails 322 provided on the upper surface of the first slide block 32 as mentioned above. Accordingly, the second slide block 33 is movable in the Y direction along the guide rails 322 by the slidable engagement of the guided grooves 331 with the guide rails 322. The chuck table mechanism 3 according to the embodiment shown in the figure further includes first indexing means 38 (first Y direction moving means) for moving the second slide block 33 in the Y direction along the guide rails 322. The first indexing means 38 includes an externally threaded rod 381 extending parallel to the guide rails 322 so as to be interposed therebetween and a pulse motor 382 as a drive source for rotationally driving the externally threaded rod 381. The externally threaded rod 381 is rotatably supported at one end thereof to a bearing block 383 fixed to the upper surface of the first slide block 32 and is connected at the other end to the output shaft of the pulse motor 382 so as to receive the torque thereof. The externally threaded rod 381 is engaged with a tapped through hole formed in an internally threaded block (not shown) projecting from the lower surface of the second slide block 33 at a central portion thereof. Accordingly, the second slide block 33 is moved in the Y direction along the guide rails 322 by operating the pulse motor 382 to normally or reversely rotate the externally threaded rod 381.

The laser beam applying unit supporting mechanism 4 includes a pair of guide rails 41 provided on the stationary base 2 so as to extend parallel to each other in the Y direction and a movable support base 42 provided on the guide rails 41 so as to be movable in the Y direction. The movable support base 42 is composed of a horizontal portion 421 slidably supported to the guide rails 41 and a vertical portion 422 extending vertically upward from the upper surface of the horizontal portion 421. Further, a pair of guide rails 423 are provided on one side surface of the vertical portion 422 so as to extend parallel to each other in the Z direction. The laser beam applying unit supporting mechanism 4 according to the embodiment shown in the figure further includes second indexing means 43 (second Y direction moving means) for moving the movable support base 42 in the Y direction along the guide rails 41. The second indexing means 43 includes an externally threaded rod 431 extending parallel to the guide rails 41 so as to be interposed therebetween and a pulse motor 432 as a drive source for rotationally driving the externally threaded rod 431. The externally threaded rod 431 is rotatably supported at one end thereof to a bearing block (not shown) fixed to the stationary base 2 and is connected at the other end to the output shaft of the pulse motor 432 so as to receive the torque thereof. The externally threaded rod 431 is engaged with a tapped through hole formed in an internally threaded block (not shown) projecting from the lower surface of the horizontal portion 421 constituting the movable support base 42 at a central portion thereof. Accordingly, the movable support base 42 is moved in the Y direction along the guide rails 41 by operating the pulse motor 432 to normally or reversely rotate the externally threaded rod 431.

The laser beam applying unit 5 includes a unit holder 51 and laser beam applying means 52 mounted to the unit holder 51. The unit holder 51 is formed with a pair of guided grooves 511 for slidably engaging the pair of guide rails 423 provided on the vertical portion 422 of the movable support base 42. Accordingly, the unit holder 51 is supported to the movable support base 42 so as to be movable in the Z direction by the slidable engagement of the guided grooves 511 with the guide rails 423.

The laser beam applying unit 5 further includes focal position adjusting means 53 (Z direction moving means) for moving the unit holder 51 along the guide rails 423 in the Z direction. The focal position adjusting means 53 includes an externally threaded rod (not shown) extending to the guide rails 423 so as to be interposed therebetween and a pulse motor 532 as a drive source for rotationally driving this externally threaded rod. Accordingly, the unit holder 51 and the laser beam applying means 52 are moved in the Z direction along the guide rails 423 by operating the pulse motor 532 to normally or reversely rotate this externally threaded rod (not shown). In this preferred embodiment shown in the figure, when the pulse motor 532 is normally operated, the laser beam applying means 52 is moved upward, whereas when the pulse motor 532 is reversely operated, the laser beam applying means 52 is moved downward.

The laser beam applying means 52 includes a cylindrical casing 521 fixed to the unit holder 51 so as to extend in a substantially horizontal direction. The configuration of the laser beam applying means 52 will now be described with reference to FIG. 2.

Figure 2:
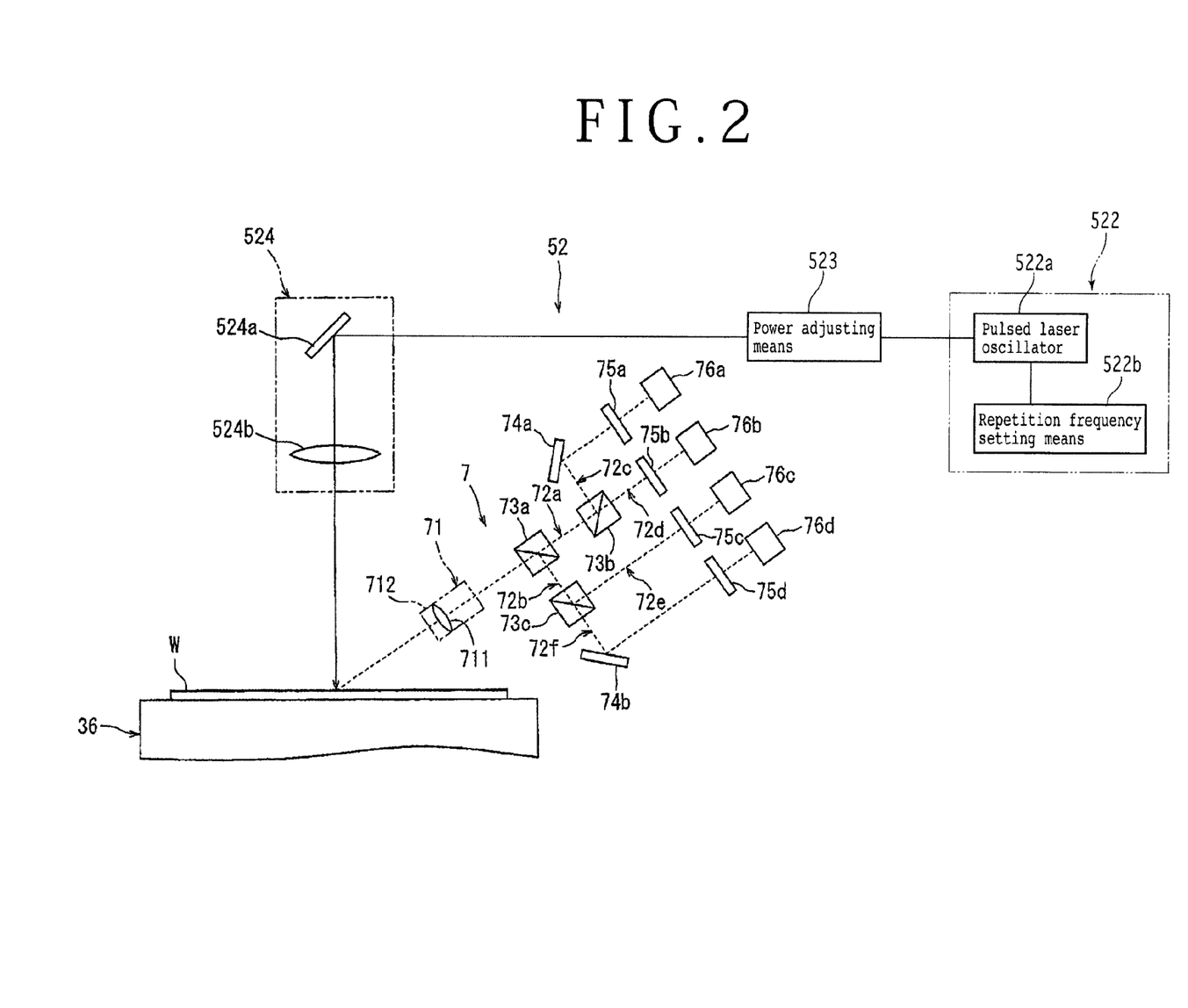
FIG. 2 is a block diagram showing the configuration of laser beam applying means and plasma detecting means included in the laser processing apparatus shown in FIG. 1.

As shown in FIG. 2, the laser beam applying means 52 includes pulsed laser beam oscillating means 522 provided in the casing 521, power adjusting means 523 for adjusting the power of a pulsed laser beam oscillated by the pulsed laser beam oscillating means 522, and focusing means 524 for applying the pulsed laser beam adjusted in power by the power adjusting means 523 to a workpiece W held on the holding surface of the chuck table 36.

The pulsed laser beam oscillating means 522 is composed of a pulsed laser oscillator 522a for oscillating a pulsed laser beam and repetition frequency setting means 522b for setting the repetition frequency of the pulsed laser beam to be oscillated by the pulsed laser oscillator 522a. The power adjusting means 523 functions to adjust the power of the pulsed laser beam oscillated by the pulsed laser beam oscillating means 522 to a predetermined power. The pulsed laser oscillator 522a and repetition frequency setting means 522b of the pulsed laser beam oscillating means 522 and the power adjusting means 523 are controlled by control means (not shown) to be hereinafter described.

The focusing means 524 includes a direction changing mirror 524a for changing the traveling direction of the pulsed laser beam oscillated by the pulsed laser beam oscillating means 522 and adjusted in power by the power adjusting means 523 toward the holding surface of the chuck table 36, and a focusing lens 524b for focusing the pulsed laser beam whose traveling direction has been changed by the direction changing mirror 524a and applying this pulsed laser beam to the workpiece W held on the chuck table 36. As shown in FIG. 1, the focusing means 524 thus-configured is mounted at the front end of the casing 521.

As shown in FIG. 1, the laser processing apparatus 1 further includes imaging means 6 provided at the front end portion of the casing 521 constituting the laser beam applying means 52 for imaging a subject area of the workpiece to be laser-processed by the laser beam applying means 52. The imaging means 6 is configured by optical means such as a microscope and a CCD camera, and an image signal output from the imaging means 6 is transmitted to the control means to be hereinafter described.

As shown in FIG. 1, the laser processing apparatus 1 further includes plasma detecting means 7 mounted on the casing 521 of the laser beam applying means 52 for detecting plasma light generated by applying the laser beam from the laser beam applying means 52 to the workpiece held on the chuck table 36. The configuration of the plasma detecting means 7 will now be described with reference to FIG. 2. As shown in FIG. 2, the plasma detecting means 7 includes plasma capturing means 71 for capturing plasma light generated by applying the laser beam from the focusing means 524 of the laser beam applying means 52 to the workpiece W held on the chuck table 36, a beam splitter 73a as branching means for branching the plasma light captured by the plasma capturing means 71 into a first optical path 72a and a second optical path 72b, a beam splitter 73b for branching the plasma light traveling along the first optical path 72a into a third optical path 72c and a fourth optical path 72d, and a beam splitter 73c for branching the plasma light traveling along the second optical path 72b into a fifth optical path 72e and a sixth optical path 72f. The plasma capturing means 71 is composed of a focusing lens 711 and a lens case 712 for accommodating the focusing lens 711. As shown in FIG. 1, the lens case 712 is mounted on the casing 521 of the laser beam applying means 52. Further, as shown in FIG. 1, the lens case 712 is provided with an angle adjusting knob 713 for adjusting the installation angle of the focusing lens 711. With this arrangement, the plasma light captured by the plasma capturing means 71 can be uniformly branched into the third optical path 72c, the fourth optical path 72d, the fifth optical path 72e, and the sixth optical path 72f.

There are provided on the third optical path 72c a direction changing mirror 74a, a first bandpass filter 75a for passing only the wavelength (251 nm) of plasma light to be generated from a set material (e.g., silicon (Si)), and a first photodetector 76a for detecting the light passed through the first bandpass filter 75a to output a light intensity signal. There are provided on the fourth optical path 72d a second bandpass filter 75b for passing only the wavelength (515 nm) of plasma light to be generated from a set material (e.g., copper (Cu)) and a second photodetector 76b for detecting the light passed through the second bandpass filter 75b to output a light intensity signal. There are provided on the fifth optical path 72e a third bandpass filter 75c for passing only the wavelength (500 nm) of plasma light to be generated from a set material (e.g., silicon dioxide ($SiO_2$)) and a third photodetector 76c for detecting the light passed through the third bandpass filter 75c to output a light intensity signal. There are provided on the sixth optical path 72f a direction changing mirror 74b, a fourth bandpass filter 75d for passing only the wavelength (545 nm) of plasma light to be generated from a set material (e.g., aluminum (Al)), and a fourth photodetector 76d for detecting the light passed through the fourth bandpass filter 75d to output a light intensity signal. The thus-configured first photodetector 76a, the second photodetector 76b, the third photodetector 76c, and the fourth photodetector 76d of the plasma detecting means 7 output to the control means voltage signals respectively corresponding to the intensities of the lights detected.

Figure 3:
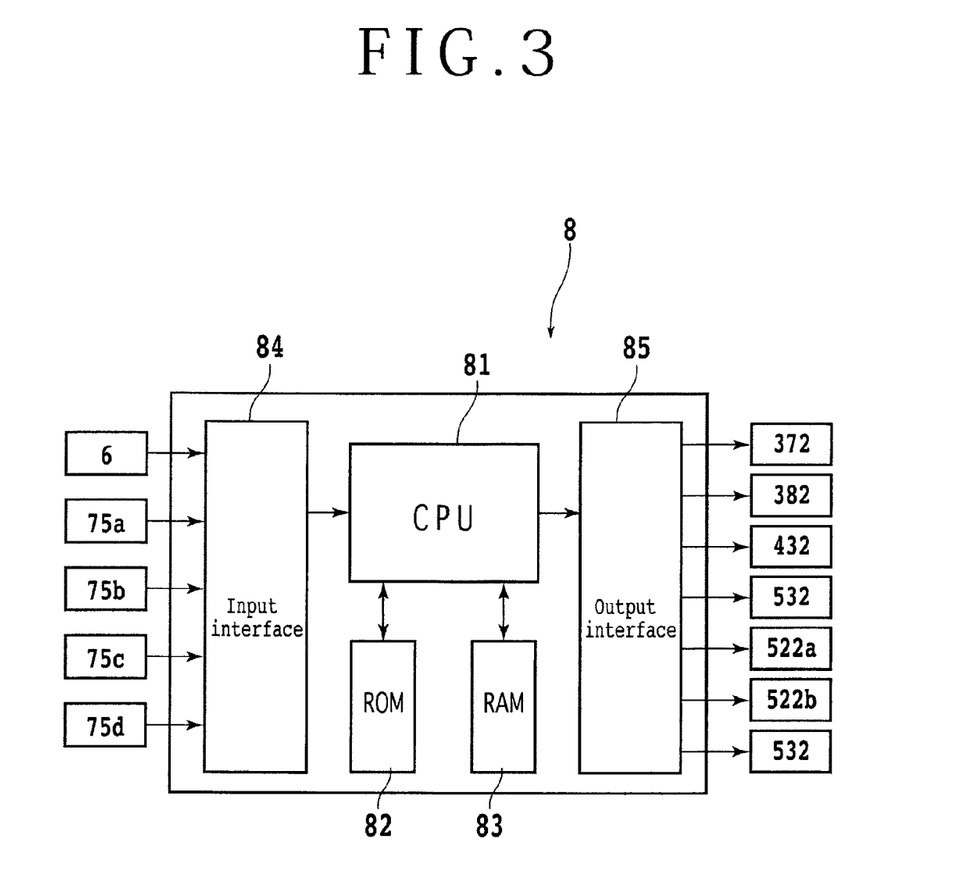
FIG. 3 is a block diagram showing the configuration of control means included in the laser processing apparatus shown in FIG. 1.
Figure 4:
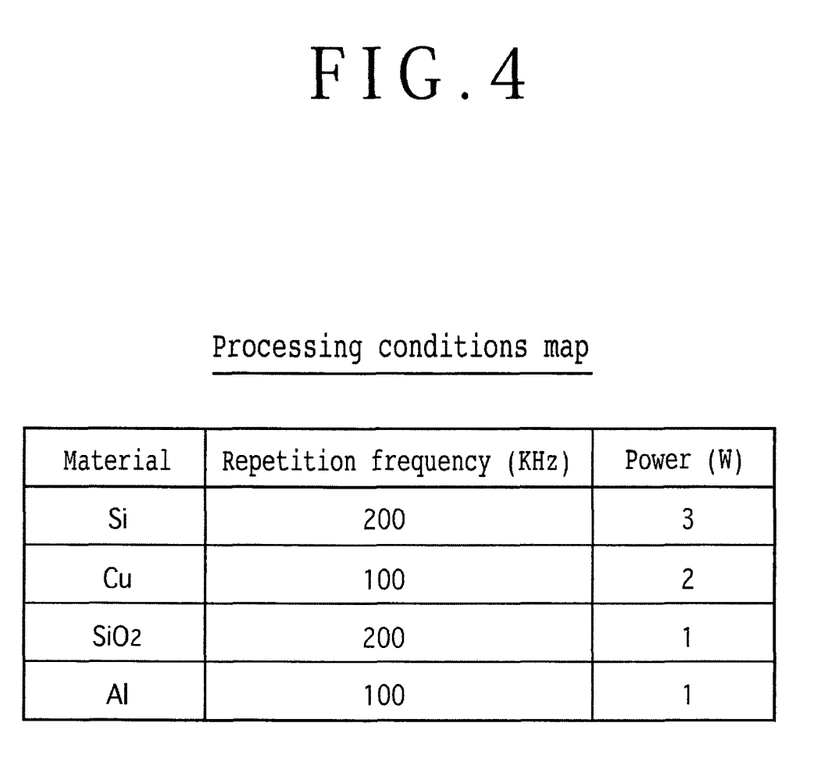
FIG. 4 is a processing conditions map stored in a memory included in the control means shown in FIG. 3.

The laser processing apparatus 1 includes the control means 8 shown in FIG. 3. The control means 8 is configured by a computer, and it includes a central processing unit (CPU) 81 for performing operational processing according to a control program, a read only memory (ROM) 82 preliminarily storing the control program, a random access memory (RAM) 83, which is readable and writable memory, for storing a control map, data on design value for the workpiece, the results of computation, etc., an input interface 84, and an output interface 85. Detection signals from the imaging means 6, the first photodetector 76a, the second photodetector 76b, the third photodetector 76c, and the fourth photodetector 76d are input into the input interface 84 of the control means 8. On the other hand, control signals are output from the output interface 85 of the control means 8 to the pulse motor 372, the pulse motor 382, the pulse motor 432, the pulse motor 532, the pulsed laser oscillator 522a and the repetition frequency setting means 522b constituting the laser beam oscillating means 522 of the laser beam applying means 52, and the power adjusting means 523. The random access memory (RAM) 83 stores a processing conditions map shown in FIG. 4, which is composed of values for the repetition frequency and power of the pulsed laser beam as set for the different materials of the plural members constituting the workpiece.

Figure 5:
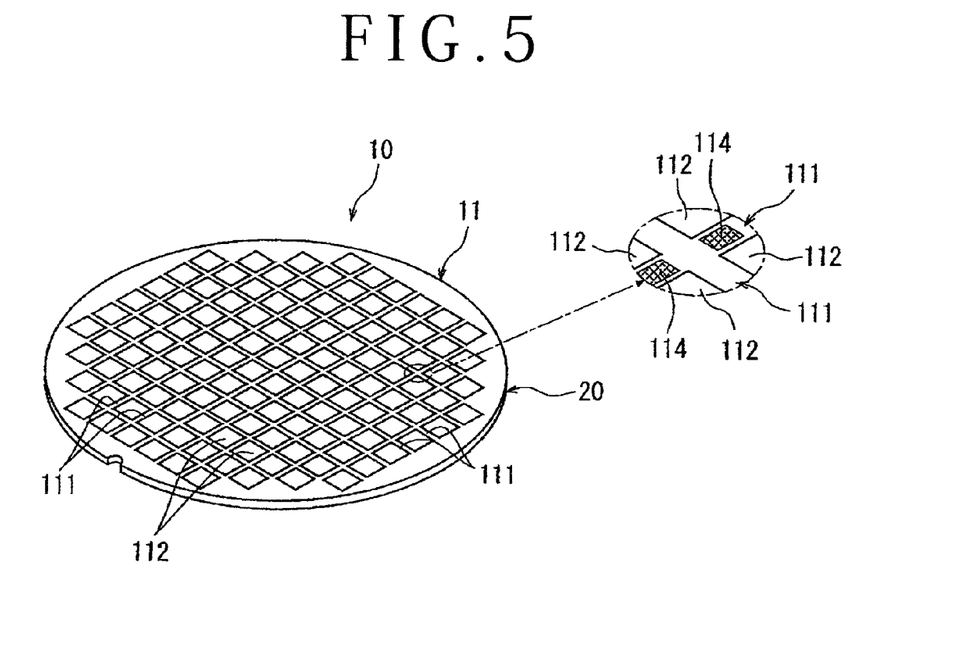
FIG. 5 is a perspective view of a semiconductor wafer as a workpiece.
Figure 6:
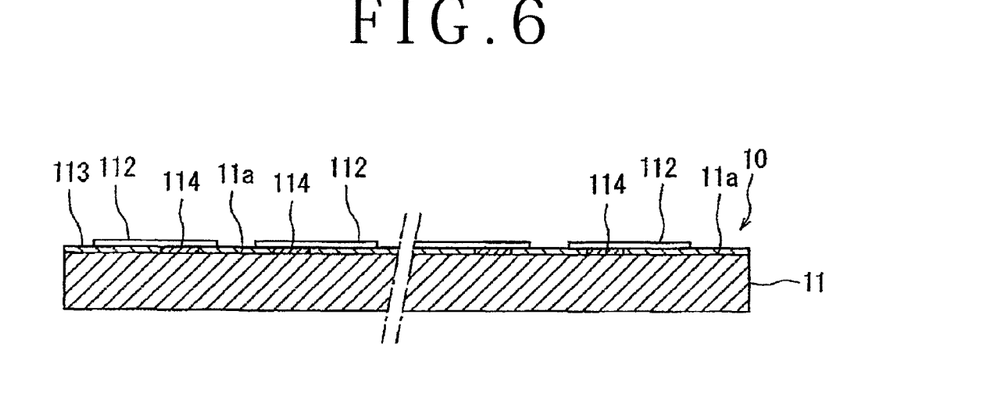
FIG. 6 is an enlarged sectional view of an essential part of the semiconductor wafer shown in FIG. 5.

The operation of the laser processing apparatus 1 configured above will now be described. FIG. 5 is a perspective view of a semiconductor wafer, and FIG. 6 is an enlarged sectional view of the semiconductor wafer cut along a street shown in FIG. 5. The semiconductor wafer 10 shown in FIGS. 5 and 6 is formed from a semiconductor substrate 11 such as a silicon wafer. A plurality of crossing streets 111 are formed on the front side 11a of the semiconductor substrate 11, thereby partitioning a plurality of rectangular regions where a plurality of devices 112 such as ICs and LSIs are respectively formed. Further, a low-permittivity insulator film 113 of silicon dioxide ($SiO_2$) is formed on the front side 11a of the semiconductor substrate 11, and a plurality of testing metal patterns 114 called test element group (Teg) made of copper (Cu) for testing the function of the devices 112 are partially provided in the streets 111.

Figure 7:
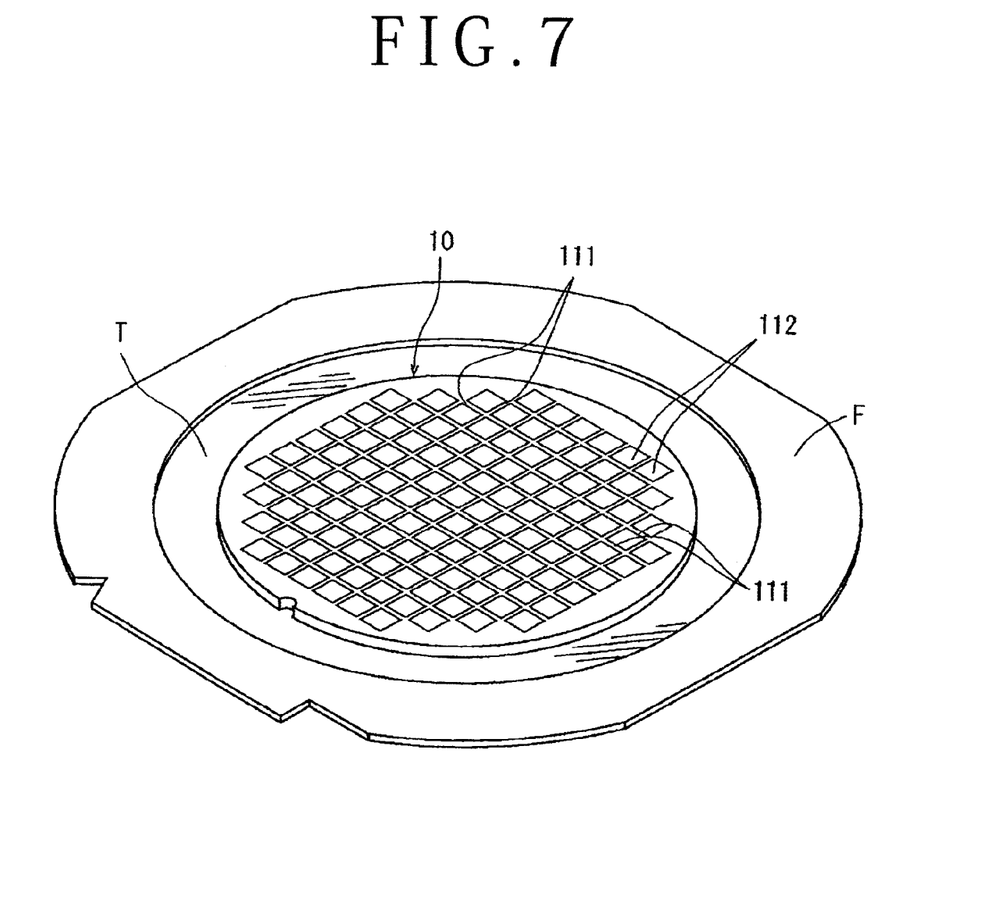
FIG. 7 is a perspective view showing a condition where the semiconductor wafer shown in FIG. 5 is attached to a protective tape supported to an annular frame.

There will now be described a method of applying a laser beam to the semiconductor wafer 10 along the streets 111 by using the laser processing apparatus to thereby form a laser processed groove along each street 111 and remove the low-permittivity insulator film 113 and the metal patterns 114 in each street 111. As shown in FIG. 7, the semiconductor wafer 10 is supported through a protective tape T to an annular frame F in such a manner that the back side of the semiconductor wafer 10 is attached to the protective tape T. The protective tape T is formed from a synthetic resin sheet such as a polyolefin sheet. Accordingly, the front side of the semiconductor wafer 10 attached to the protective tape T is oriented upward. The semiconductor wafer 10 supported through the protective tape T to the annular frame F is placed on the chuck table 36 of the laser processing apparatus 1 shown in FIG. 1 in the condition where the protective tape T comes into contact with the upper surface of the chuck table 36. Thereafter, the suction means (not shown) is operated to hold the semiconductor wafer 10 through the protective tape T on the chuck table 36 under suction. Accordingly, the semiconductor wafer 10 is held on the chuck table 36 in the condition where the front side of the semiconductor wafer 10 is oriented upward. Further, the annular frame F is fixed by the clamps 362.

Thereafter, the feeding means 37 is operated to move the chuck table 36 holding the semiconductor wafer 10 under suction to a position directly below the imaging means 6. In the condition where the chuck table 36 is positioned directly below the imaging means 6, the control means 8 operates the imaging means 6 to perform an alignment operation for detecting a subject area of the semiconductor wafer 10 to be laser-processed. More specifically, the imaging means 6 and the control means 8 perform image processing such as pattern matching for making the alignment of the streets 111 extending in a first direction on the semiconductor wafer 10 and the focusing means 524 of the laser beam applying means 52, thus performing the alignment of a laser beam applying position. The imaging means 6 and the control means 8 similarly perform the alignment operation for the other streets 111 extending in a second direction perpendicular to the first direction mentioned above on the semiconductor wafer 10.

Figure 8A:
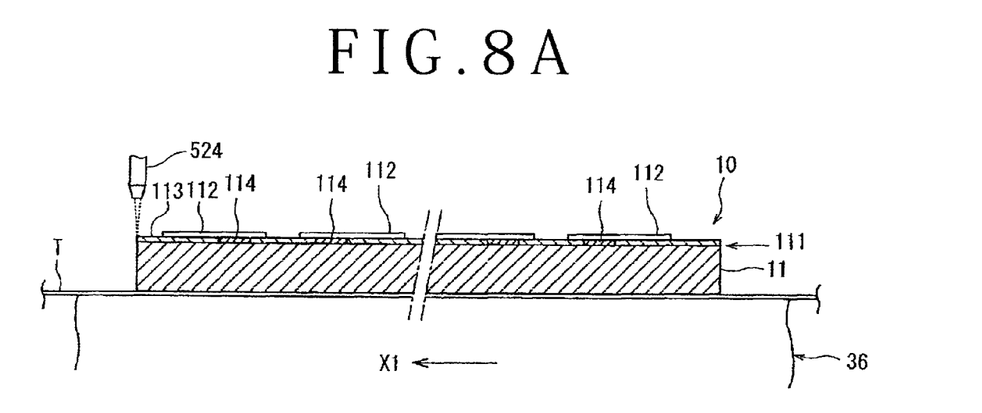
FIGS. 8A and 8B are partially cutaway sectional side views for illustrating a laser processing step to be performed by the laser processing apparatus shown in FIG. 1.

Next, the chuck table 36 is moved to a position where one end (left end as viewed in FIG. 8A) of a predetermined one of the streets 111 extending in the first direction is positioned directly below the focusing means 524 as shown in FIG. 8A. Thereafter, the control means 8 outputs a control signal to the laser beam applying means 52 to apply a pulsed laser beam having an absorption wavelength (355 nm) to the low-permittivity insulator film 113 and the metal patterns 114 at a predetermined pulse width (30 ns, for example) from the focusing means 524 to the semiconductor wafer 10, and the chuck table 36 is moved in the direction shown by an arrow X1 at a predetermined feed speed (100 mm/s) (laser processing step).

In this laser processing step, the control means 8 inputs the light intensity signals from the first photodetector 76a, the second photodetector 76b, the third photodetector 76c, and the fourth photodetector 76d of the plasma detecting means 7. At starting the laser processing step in the condition where one end (left end as viewed in FIG. 8A) of the predetermined street 111 is positioned directly below the focusing means 524 as shown in FIG. 8A, it is determined that the area to be first laser-processed is the low-permittivity insulator film 113. Accordingly, the control means 8 controls the repetition frequency setting means 522b and the power adjusting means 523 of the laser beam applying means 52 according to the processing conditions map shown in FIG. 4, which is stored in the random access memory (RAM) 83, so that the repetition frequency of the pulsed laser beam becomes 200 kHz and the power of the pulsed laser beam becomes 1 W so as to correspond to silicon dioxide ($SiO_2$) forming the low-permittivity insulator film 113. When the pulsed laser beam is applied to the low-permittivity insulator film 113, plasma light having a wavelength of 500 nm is generated. This plasma light having a wavelength of 500 nm is focused by the focusing lens 711 of the plasma capturing means 71 constituting the plasma detecting means 7 shown in FIG. 2, next branched by the beam splitters 73a, 73b, and 73c, next changed in traveling direction by the direction changing mirrors 74a and 74b, and next reaches the first bandpass filter 75a, the second bandpass filter 75b, the third bandpass filter 75c, and the fourth bandpass filter 75d. However, the plasma light is allowed to pass only the third bandpass filter 75c for passing only the wavelength (500 nm) of plasma light to be generated from silicon dioxide ($SiO_2$). The plasma light passed through the third bandpass filter 75c is detected by the third photodetector 76c, and a voltage signal corresponding to the light intensity detected by the third photodetector 76c is transmitted to the control means 8. The control means 8 determines that the voltage signal from the third photodetector 76c is due to the plasma light generated from silicon dioxide ($SiO_2$) and continues the above control such that the repetition frequency and power of the pulsed laser beam are set to 200 kHz and 1 W, respectively.

When a predetermined one of the metal patterns 114 reaches the position directly below the focusing means 524 and the pulsed laser beam is applied to this predetermined metal pattern 114, plasma light having a wavelength of 515 nm is generated. This plasma light having a wavelength of 515 nm is focused by the focusing lens 711 of the plasma capturing means 71 constituting the plasma detecting means 7 shown in FIG. 2, next branched by the beam splitters 73a, 73b, and 73c, next changed in traveling direction by the direction changing mirrors 74a and 74b, and next reaches the first bandpass filter 75a, the second bandpass filter 75b, the third bandpass filter 75c, and the fourth bandpass filter 75d. However, the plasma light is allowed to pass only the second bandpass filter 75b for passing only the wavelength (515 nm) of plasma light to be generated from copper (Cu). The plasma light passed through the second bandpass filter 75b is detected by the second photodetector 76b, and a voltage signal corresponding to the light intensity detected by the second photodetector 76b is transmitted to the control means 8. The control means 8 determines that the voltage signal from the second photodetector 76b is due to the plasma light generated from copper (Cu) and then controls the repetition frequency setting means 522b and the power adjusting means 523 of the laser beam applying means 52 according to the processing conditions map shown in FIG. 4, which is stored in the random access memory (RAM) 83, so that the repetition frequency of the pulsed laser beam becomes 100 kHz and the power of the pulsed laser beam becomes 2 W so as to correspond to copper (Cu) forming the metal patterns 114. When the low-permittivity insulator film 113 reaches the position directly below the focusing means 524 again and the pulsed laser beam is applied to the low-permittivity insulator film 113, plasma light having a wavelength of 500 nm is generated again. Accordingly, the control means 8 controls the repetition frequency setting means 522b and the power adjusting means 523 of the laser beam applying means 52 so that the repetition frequency and power of the pulsed laser beam become 200 kHz and 1 W, respectively, so as to correspond to silicon dioxide ($SiO_2$) forming the low-permittivity insulator film 113.

Figure 8B:
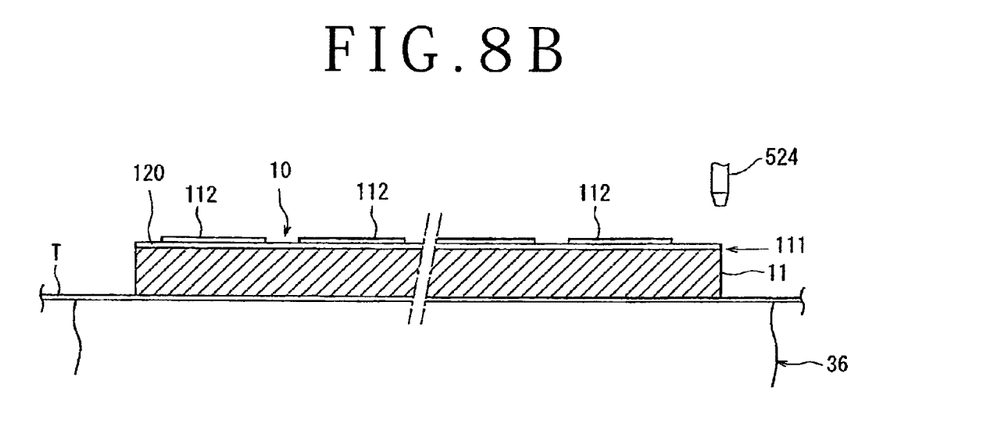

In this manner, every time the pulsed laser beam is alternately applied to the low-permittivity insulator film 113 and the metal pattern 114 to generate the plasma light having the wavelengths respectively corresponding to the low-permittivity insulator film 113 and the metal pattern 114, the control means 8 controls the repetition frequency and power of the pulsed laser beam so that they are suitable for silicon dioxide ($SiO_2$) forming the low-permittivity insulator film 113 and copper (Cu) forming the metal pattern 114. Accordingly, even in the case that the low-permittivity insulator film 113 and the metal pattern 114 are mixedly present on the semiconductor substrate 11, laser processing can be performed to the semiconductor wafer 10 under the processing conditions individually suitable for the low-permittivity insulator film 113 and the metal pattern 114 without making coordinate data for the low-permittivity insulator film 113 and the metal pattern 114. When the other end (right end as viewed in FIG. 8B) of the predetermined street 111 reaches the position directly below the focusing means 524 as shown in FIG. 8B, the application of the pulsed laser beam is stopped (laser processed groove forming step). As a result, a laser processed groove 120 having a depth reaching the semiconductor substrate 11 is formed along the predetermined street 111 on the semiconductor wafer 10, and the metal patterns 114 and the low-permittivity insulator film 113 are removed along the predetermined street 111 on the semiconductor wafer 10 as shown in FIG. 8B.

While laser processing is performed on the workpiece configured so that the low-permittivity insulator film 113 of silicon dioxide ($SiO_2$) and the metal patterns 114 of copper (Cu) are formed so as to be exposed to each street 111 in the above preferred embodiment, the power of the laser beam can be controlled similarly also in the case that silicon (Si) and aluminum (Al) are exposed to each street.

The present invention is not limited to the details of the above described preferred embodiments. The scope of the invention is defined by the appended claims and all changes and modifications as fall within the equivalence of the scope of the claims are therefore to be embraced by the invention.

What is claimed is:

1. A laser processing method of applying a pulsed laser beam to a workpiece having a plurality of members, thereby forming a laser processed groove on said workpiece, said laser processing method comprising:
    a processing conditions setting step of setting a plurality of processing conditions respectively corresponding to a plurality of different materials forming said plurality of members constituting said workpiece, wherein said processing conditions setting step includes storing, in a memory, a processing conditions map in which a plurality of said different materials are each mapped to both a repetition frequency of the pulsed laser and a power of the pulsed laser;
    a wavelength detecting step of detecting the wavelengths of plasma lights generated by applying said pulsed laser beam to said plurality of members constituting said workpiece;
    a processing condition selecting step of selecting, from said processing conditions map, any suitable one of said processing conditions corresponding to any one of said members corresponding to the wavelength of plasma lights detected by said wavelength detecting step; and
    a laser processing step of applying said pulsed laser beam to said workpiece under the processing condition selected by said processing condition selecting step, thereby forming said laser processed groove on said workpiece,
    wherein said plurality of different materials comprises four different materials, defined as a first material, a second material, a third material and a fourth material; and
    wherein said wavelength detecting step comprises:
        directing plasma light generated by applying said pulsed laser beam to a first beam splitter that branches said plasma light into a first path and a second path;
        directing said first path of said plasma light to a second beam splitter that branches said first path into a third path and a fourth path;
        directing said second path of plasma light to a third beam splitter that branches said second path into a fifth path and a sixth path;
        directing said third path of said plasma light through a first bandpass filter corresponding to a first wavelength, and then directing any plasma light corresponding to said first wavelength passing through said first bandpass filter to a first photodetector;
        directing said fourth path of said plasma light through a second bandpass filter corresponding to a second wavelength, and then directing any plasma light corresponding to said second wavelength passing through said second bandpass filter to a second photodetector;
        directing said fifth path of said plasma light through a third bandpass filter corresponding to a third wavelength, and then directing any plasma light corresponding to said third wavelength passing through said third bandpass filter to a third photodetector; and
        directing said sixth path of said plasma light through a fourth bandpass filter corresponding to a fourth wavelength, and then directing any plasma light corresponding to said fourth wavelength passing through said fourth bandpass filter to a fourth photodetector;
    wherein said first wavelength corresponds to said first material, said second wavelength corresponds to said second material, said third wavelength corresponds to said third material, and said fourth wavelength corresponds to said fourth material.

2. A laser processing apparatus comprising:
    workpiece holding means for holding a workpiece;
    laser beam applying means for applying a pulsed laser beam to said workpiece held by said workpiece holding means, said laser beam applying means including laser beam oscillating means for oscillating a pulsed laser beam, a repetition frequency setting means for setting the repetition frequency of said pulsed laser beam to be oscillated by said laser beam oscillating means, power adjusting means for adjusting the power of said pulsed laser beam oscillated by said laser beam oscillating means, and focusing means for focusing said pulsed laser beam adjusted in power by said power adjusting means;
    feeding means for relatively feeding said workpiece holding means and said laser beam applying means;
    plasma detecting means for detecting the wavelength of plasma light generated by applying said pulsed laser beam from said laser beam applying means to said workpiece held by said wavelength holding means; and
    control means for controlling said laser beam applying means according to a detection signal from said plasma detecting means;
    said plasma detecting means including:

branching means for branching said plasma light into a plurality of optical paths;
a plurality of bandpass filters respectively provided on said plurality of optical paths for respectively passing only the specific wavelengths of plasma lights generated from a plurality of different materials forming a plurality of members constituting said workpiece; and
a plurality of photodetectors for respectively detecting the lights passed through said plurality of bandpass filters and outputting light intensity signals to said control means;
said control means having a memory storing a processing conditions map setting a plurality of processing conditions respectively corresponding to said plurality of different materials;
said control means selecting any suitable one of said processing conditions set on the processing conditions map according to the detection signals from said plurality of photodetectors and then controlling said laser beam applying means under the processing condition selected above,
wherein said processing conditions map involves mapping each of said plurality of different materials to both a repetition frequency of the pulsed laser and a power of the pulsed laser; and
said control means controls said power adjusting means so that the power of said pulsed laser beam becomes a suitable one of said powers set on said processing conditions map according to the detection signals from said plurality of photodetectors photodetectors,
wherein said plurality of different materials comprises four different materials, defined as a first material, a second material, a third material and a fourth material; and
wherein said laser processing apparatus further comprises:
a first beam splitter that branches said plasma light into a first path and a second path;
a second beam splitter that branches said first path into a third path and a fourth path;
a third beam splitter that branches said second path into a fifth path and a sixth path;
a first bandpass filter for receiving said third path of said plasma light, wherein said first bandpass filter corresponds to a first wavelength, and wherein plasma light corresponding to said first wavelength passes through said first bandpass filter to a first photodetector;
a second bandpass filter for receiving said fourth path of said plasma light, wherein said second bandpass filter corresponds to a second wavelength, and wherein plasma light corresponding to said second wavelength passes through said second bandpass filter to a second photodetector;
a third bandpass filter for receiving said fifth path of said plasma light, wherein said third bandpass filter corresponds to a third wavelength, and wherein plasma light corresponding to said third wavelength passes through said third bandpass filter to a third photodetector; and
a fourth bandpass filter for receiving said sixth path of said plasma light, wherein said fourth bandpass filter corresponds to a fourth wavelength, and wherein plasma light corresponding to said fourth wavelength passes through said fourth bandpass filter to a fourth photodetector,
wherein said first wavelength corresponds to said first material, said second wavelength corresponds to said second material, said third wavelength corresponds to said third material, and said fourth wavelength corresponds to said fourth material.

3. The laser processing apparatus according to claim 2, wherein said control means controls said repetition frequency setting means so that the repetition frequency of said pulsed laser beam becomes a suitable one of said repetition frequencies set on said processing conditions map according to the detection signals from said plurality of photodetectors.

* * * * *